United States Patent [19]

Warriner

[11] Patent Number: Plant 6,667

[45] Date of Patent: Mar. 14, 1989

[54] ROSE PLANT JACCOB

[75] Inventor: William A. Warriner, Tustin, Calif.

[73] Assignee: Jackson & Perkins Company, Medford, Oreg.

[21] Appl. No.: 87,251

[22] Filed: Aug. 18, 1987

[51] Int. Cl.[4] ..... A01H 5/00

[52] U.S. Cl. ..... Plt./17

[58] Field of Search ..... Plt./16–17

*Primary Examiner*—Robert E. Bagwill

*Attorney, Agent, or Firm*—Majestic, Gallagher, Parsons & Siebert

[57] ABSTRACT

A rose variety of the hybrid tea class is provided having unusual orange and yellow blend flower color blooms heavily produced on long cutting stems with large and small prickles and many prickles on petiole rachis.

1 Drawing Sheet

SUMMARY OF THE INVENTION

The present invention relates to a new and distinct variety of rose plant of the hybrid tea class, which was originated by me by crossing an unnamed seedling with an unnamed seedling.

The primary objective of this breeding was to produce a new rose variety of the hybrid tea class exhibiting large, attractive and brightly colored blossoms on long stems. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. High production of large hybrid tea flowers;
2. Long cutting stems;
3. Upright, vigorous plant;
4. Many prickles on petiole rachis;
5. Large and small prickles on stem;
6. Unusual orange and yellow blend flower color.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jaccob". Color terminology is in accordance with The Royal Horticultural Society Colour Chart except where an ordinary dictionary significance for the color is apparent.

Observations of the buds and flowers were made from specimens grown in a garden at Irvine, Calif. in July.

FLOWER

The blooming habit is continuous. The bud size is one and one-half inches when the petals start to unfurl. The bud form is pointed ovoid. The bud color when sepals first divide is near Orange-Red Group 32B blending to Yellow-Orange Group 23B to near Yellow Group 12B going from the top to the base of the petal. When half blown, the upper side of petals is near Orange-Red Group 32B to 32C, and the lower side of petals is near Orange-Red Group 32D blending to near Yellow Group 12B at the base. The sepals have a color near Green Group 138B. The surface texture is covered with very fine hairs and with glands. There are three appendaged sepals normally appendaged, and two unappendaged sepals with hairy edge. The receptacle color is bronze and green with a funnel shape, large size and hairy surface. The peduncle is medium, and has a glandular surface. Peduncle color is bronzy and the penduncle is stiff, erect and heavy.

BLOOM

Bloom size is large, with an average open size of five inches, borne singly. The stems are strong and long. The form when first open is high center. The petals retain their form to the end with the outer petals curling back, with some quilling. Under normal conditions there are 25 to 30 petals. The upper side of petals is near Orange-Red Group 32B to 32C, and the reverse side of the petals is near Orange-Red Group 32D blending to near Yellow Group 12B at the base of the petal. The base of petals has a small yellow half-moon (near Yellow Group 12B). The major color is near Orange-Red Group 32B to 32C. There are occasional streaks on the outside petals. The general tonality at the end of the first day shows no change in color. At the end of the third day, there is some fading in bright sunlight to near Orange-Red Group 32D.

The fragrance is slight. The petal texture is thick, of a round to oval, deltoid shape, and the form is flat with tips slightly recurved and the edges slightly quilled.

The arrangement is imbricated with few petaloids in the center. The blooms drop off cleanly, and last on the plant for a long period and as a cut flower for a long time.

Reproductive Parts

The anthers are large, of yellow color, arranged regularly around the styles and are mixed with occasional petaloids. The filaments are yellow, the pollen is gold yellow, the styles are red, and the stigmas are greenish white.

Plant

A vigorous, upright growth of bush form.

Foliage

Large size, normal in quantity. The new foliage is bronze colored that turns dark glossy green as old foliage. Normal mid-stem leaves have five leaflets (occasionally seven).

The leaflets are broadly oval, are leathery and glossy, and have a serrated edge. The serration is single and small in size. Petiole rachis is reddish, and petiole underside is rough with many prickles. Stipules are short and edged with glands. The foliage is susceptible to mildew under normal growing conditions at Irvine, Calif.

Wood

New wood is reddish, with a smooth bark. Old wood is green with a smoth bark.

Prickles

There are many prickles on main canes from the base and on laterals from the main canes. The form is medium and hooked downward. Color when young is red.

Parentage

The seed parent was an unnamed seedling. The pollen parent was an unnamed seedling.

Classification

Botanical is rosa hybrid. Commercial is hybrid tea.

I claim:

1. A new and distinct variety of rose plant and parts thereof of the hybrid tea class substantially as herein shown and described, characterized particularly as to novelty by an unusual orange and yellow blend flower color, heavy flower production on long stems, presence of large and small prickles on flower stems and presence of prickles on rachis.

* * * * *

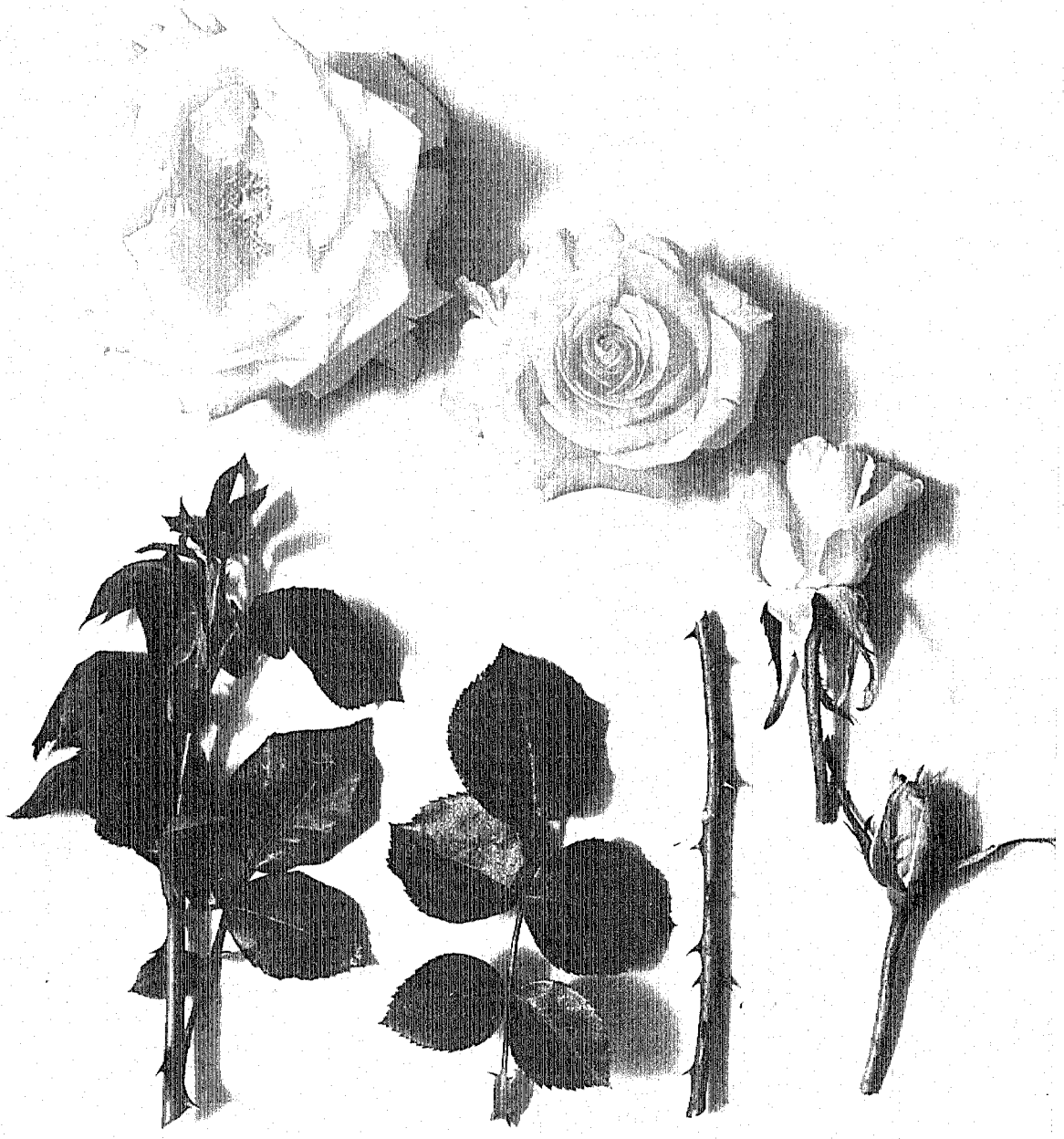
Jacob